US006221377B1

(12) United States Patent
Meyer

(10) Patent No.: US 6,221,377 B1
(45) Date of Patent: Apr. 24, 2001

(54) ADMINISTRATION MEDIA FOR ANALGESIC, ANTI-INFLAMMATORY AND ANTI-PYRETIC DRUGS CONTAINING NITROUS OXIDE AND PHARMACEUTICAL COMPOSITIONS CONTAINING SUCH MEDIA AND DRUGS

(75) Inventor: Petrus Johannes Meyer, Randburg (ZA)

(73) Assignee: Pitmy International N.V., Bonaire (NL)

( * ) Notice: Subject to any disclaimer, the term of this patent is extended or adjusted under 35 U.S.C. 154(b) by 0 days.

(21) Appl. No.: 09/068,543
(22) PCT Filed: Nov. 13, 1996
(86) PCT No.: PCT/IB96/01366
  § 371 Date: May 13, 1998
  § 102(e) Date: May 13, 1998
(87) PCT Pub. No.: WO97/17978
  PCT Pub. Date: May 22, 1997

(30) Foreign Application Priority Data

Nov. 13, 1995 (ZA) .................................................. 95/9609

(51) Int. Cl.[7] ...................................................... A61F 13/00
(52) U.S. Cl. ................... 424/434; 514/177; 514/212.01; 514/291; 514/307; 514/315; 514/352; 514/412; 514/415; 514/374; 514/365; 514/410; 514/418; 514/419; 514/423; 514/428; 514/430; 514/450; 514/539; 514/558; 514/567; 514/569; 514/570
(58) Field of Search ..................................... 514/560, 718, 514/825, 859, 861, 863, 880, 177, 212.01, 291, 307, 315, 352, 365, 374, 410, 412, 415, 418, 419, 423, 428, 430, 450, 539, 558, 567, 569, 570

(56) References Cited

FOREIGN PATENT DOCUMENTS 2 277 264  10/1994  (GB) .

OTHER PUBLICATIONS

Chemical ABstracts AN 1985:464783, Hertz et al., Jan. 1985.*
Chemical Abstracts AN 1978:44978, Berkowitz et al., Jan. 1977.*
International Publication No. WO 93/25213, published Dec. 23, 1993.
Mikrochim. Acta, vol. 2, No. 5–6, 1980 pp. 464–474, Stahl et al., Extraction of natural substances using supercritical and liquified gases.
Reynolds J.E.F. et al., "Martindale", 1989, The Pharmaceutical Press.
Science, vol. 194, No. 4268, 1976, pp. 967–968, Berkowitz et al., "Nitrous oxide "analgesia": resemblance to opiate action".
Steinegger et al., "Lehrbuch der Pharmakognosie und Phytopharmazie", Edition 4, 1988.

* cited by examiner

Primary Examiner—Jyothsna Venkat
Assistant Examiner—Grace Hsu
(74) Attorney, Agent, or Firm—Arent Fox Kintner Plotkin & Kahn PLLC

(57) ABSTRACT

Administration mediums comprising solutions of nitrous oxide in water, alcohols, ethers or oils, and optionally including essential fatty acids or $C_1$–$C_6$ alkyl esters thereof enhance the action of analgesic, anti-inflammatory and anti-pyretic drugs. The drugs may be combined with the medium into a pharmaceutical composition or may be taken orally by swallowing the drug with the aid of the medium.

49 Claims, No Drawings

ADMINISTRATION MEDIA FOR ANALGESIC, ANTI-INFLAMMATORY AND ANTI-PYRETIC DRUGS CONTAINING NITROUS OXIDE AND PHARMACEUTICAL COMPOSITIONS CONTAINING SUCH MEDIA AND DRUGS

FIELD OF THE INVENTION

THIS invention relates to novel preparations of analgesic, anti-inflammatory and anti-pyretic agents. More particularly, this invention relates to the enhancement of the efficacy of such agents.

BACKGROUND TO THE INVENTION

[a] Analgesic, Anti-inflammatory and Anti-pyretic Drugs

Non-narcotic analgesics, most of which are also known as non-steroidal anti-inflammatory drugs [NSAID], are widely administered orally in the treatment of mild to severe pain. Within this class, the compounds vary widely in their chemical structure and in their biological profiles as analgesics, anti-inflammatory agents and anti-pyretic agents. Aspirin, acetaminophen and phenacetin have long been among the most commonly used members of this group; more recently, however, a large number of alternative non-narcotic agents offering a variety of advantages over the earlier drugs have been developed. Tolerance or addiction to these drugs is not generally a problem with their continuous use in the treatment of pain or in the treatment of acute or chronic inflammatory states [notably, rheumatoid arthritis and osteoarthritis]; nevertheless, these drugs generally have a higher potential for adverse side-effects at the upper limits of their effective dose ranges. Moreover, above each drug's upper limit or ceiling, administration of additional drugs does not usually increase the analgesic or anti-inflammatory effect. Among the newer compounds in the non-narcotic analgesic/non-steroidal anti-inflammatory group are compounds such as diflunisal [Dolobid®], ibuprofen [Brufen®], naproxen [Naprosyn®], fenoprofen [Fenopron®], piroxicam [Feldene®], flurbiprofen, mefenamic acid [Ponstan®] and sulindac [Clinoril®]. See also *Physicans' Desk Reference*, 35th edition, 1981, and *The Merck Index*, ninth edition, Merck & Co., Rahway, New Jersey (1976), for information on specific non-steroidal anti-inflammatory agents. Also see, generally, Wiseman, *"Pharmacological Studies with a New Class of Non-steroidal Anti-Inflammatory Agents—Tbe Oxicams—With Special Reference to Piroxicam (Feldene®)"*, The American Journal of Medicine, Feb. 16, 1982:2–8; Foley et al, *The Management of Cancer Pain, Volume II—The Rational Use of Analgesics in the Management of Cancer Pain*, Hoffman-La Roche Inc., 1981; and *Cutting's Handbook of Pharmacology*, sixth edition, ed. T. Z. Czáky, M.D. Appleton-Century-Crofts, New York, 1979, Chapter 49: 538–550.

The exact mechanism of action of this group of compounds and the relationship between chemical structure and analgesic, anti-inflammatory and anti-pyretic effect of these compounds are not yet fully understood despite the fact that some of these products, like aspirin and acetaminophen have been in use for many years. The recent contributions of John Vane in "Towards a better aspirin", *Nature* Volume 367, Jan. 20, 1993, pages 215 to 216 and of the authors referred to therein, which links such activities to the ability of these compounds to inhibit the enzyme known as cyclooxygenase [COX] of which two, and possibly three, isoforms exist, will no doubt play an important role in the future understanding of the mode of action and properties of this group of compounds.

Narcotic analgesics are often used when pain control with non-narcotic analgesics is ineffective. While the drugs in this group vary considerably in their chemical structures and pharmacological properties, almost all suffer the disadvantages of tolerance and possible addiction with continued usage. Within the narcotic analgesic group, the drugs can be classified as narcotic agonists or narcotic antagonists. Narcotic agonists include the morphine group, the pethidine group and the methadone group. While some narcotic antagonists are pure antagonists [which are not analgesics], other narcotic antagonists are agonist-antagonists [i.e. antagonists with analgesic properties]; the agonist-antagonists are generally categorised as morphine-like or nalorphine-like]. Many of the narcotic analgesics are not effective orally, but are rather used parenterally. The orally active narcotic analgesics include such compounds as codeine, oxycodone, pethidine, dextro-propoxyphene [Doloxene®], methadone, propiram, buprenorphine, pentazocine [Sosegon®] and nalbuphine [Nubain®]. For more specific information on these compounds, see *Physicians' Desk Reference*, 35th edition, 1981, and *The Merck Index*, ninth edition, Merck & Co., Inc., Rahway, New Jersey 1976). Also see, generally, the Foley et al reference cited hereinabove and *Cutting's Handbook of Pharacology*, sixth edition, ed. T. Z. Czáky, M.D., Appleton-Century-Crofts, New York, 1979, Chapter 50: 551–566.

[b] Potentiation of Analgesic, Anti-inflammatory and Anti-pyretic Drugs

It has been suggested in South African Patent 83/5324 in the name of Sunshine, Laska and Siegel that caffeine may be used to hasten the onset and to enhance the analgesic response of the analgesic, anti-inflammatory and anti-pyretic agents referred to above.

[c] Nitrous Oxide Gas

Nitrous oxide [$N_2O$] is a natural gas which is also produced synthetically. It is also known by the trivial name "laughing gas". It has been in use for many years as an inhalation anaesthetic and analgesic, particularly in dentistry.

Nitrous oxide has been reported to have a synergistic or potentiating effect on halothane and other gaseous anaesthetics [See *Goodman & Gilman's The Pharmacological Basis of Therapeutics* 8th Ed. 1990 pp. 298–300].

Since such known synergism or potentiation is based on the use of nitrous oxide administered by inhalation, and since the use of nitrous oxide on its own as an anaesthetic and analgesic has likewise been in the form of an inhalation agent, the use of nitrous oxide for all these purposes have been confined to hospitalised patients or, at best, to treatments carried out by medical practitioners in their consulting rooms, or treatments carried out by or under supervision of a nurse in charge of a home-care patient.

[d] Nitrous Oxide in Solution

Nitrous oxide is known to be soluble in water and it has been reported that at 20° C. and 2 atm pressure one litre of the gas dissolves in 1,5 litres of water, see *The Merck Index* 10th Ed. p. 6499.

In the applicant's PCT patent application PCT/EP93/01405 published under number WO 93/25213 and co-pending patent applications derived therefrom and its South African counterpart Patent 94/3895 it disclosed dermatological compositions comprising nitrous oxide as an active ingredient in compositions which also include one or more essential fatty acids or lower alkyl esters thereof, and, optionally, one or more supplementary active ingredients selected from the group consisting of coal tar solution, collagen, lanolin, nicotinamide, nicotinic acid, lanolin, vitamin E, methyl salicylate, arnica and an H-antagonist antihistamine such as diphenylhydramine hydrochloride. In those compositions nitrous oxide is dissolved in water.

Nitrous oxide is also known for its use as a propellant gas, mainly as a substitute for propellant gases such as chlorofluorocarbons, and more particularly to produce a food product mousse such as whipped cream or chocolate mousse or quick-breaking foams for hair treatment preparations. See in this regard U.K. Patent 1033299, U.K. Patent 1105919 and European Patent Application EPA-0123827. None of these prior publications suggest that the nitrous oxide gas, plays any other role than a physical one, i.e. to expand on being depressurised and thereby to create a mousse or a foam. In fact it is typically regarded as an inert in these applications and useful due to the fact that it is colourless, odourless and tasteless but soluble in water and oils.

There appears to be no suggestion in the literature that aqueous solutions of nitrous oxide might have any analgesic or anaesthetic effect on man or animals. As far as the present inventors know it has also never been suggested that nitrous oxide may be used in conjunction with analgesic, anti-inflammatory or anti-pyretic substances to contribute to, or to hasten or to enhance their pharmacological action.

SUMMARY OF THE INVENTION

It has now unexpectedly been found that there is a surprisingly simple manner for utilising nitrous oxide to enhance the efficacy of analgesic, anti-inflammatory and/or anti-pyretic substances.

According to the present invention there is provided an administration medium for use in conjunction with a medicament selected from the group consisting of the analgesic, anti-inflammatory and anti-pyretic substances to enhance the pharmacological action of such substances, the medium comprising a solution of nitrous oxide in a pharmaceutically acceptable carrier solvent.

The carrier solvent may be water or any of the pharmaceutically acceptable alcohols, ethers or oils. The oil may be an organic or mineral oil. The organic oil may be an essential oil based on long chain fatty acids having between 14 and 20 carbon atoms in the fatty acid. The oil may also be of either natural or synthetic origin and, if of natural origin, it may be either a plant oil or an animal oil. As plant oils those rich in gamma linolenic acid [GLA] are preferred and as animal oil dairy cream may be used.

In the preferred form of the invention the administration medium comprises water which is saturated with nitrous oxide.

When used in conjunction with a medicament which is to be administered to a patient in a solid oral dosage form such as powders, tablets or capsules, the potentiating or synergistic administration medium may simply comprise a quantity of water charged with nitrous oxide gas used to swallow the medicament. In this form the water may, of course, include dissolved salts of the type conventionally found in potable water. Preferably, however, the water is deionised water.

When the medicament to be potentiated or synergised by means of the nitrous oxide is in a liquid formulation, such formulation may incorporate water or acceptable other liquid solvent into which the nitrous oxide had been dissolved. Likewise, where the medicament is to be administered to the patient by being applied as a topical, buccal or vaginal cream or ointment or as an intravenous, intramuscular or subcutaneous injection or as a suppository the formulation used in making up such cream, ointment, injectable formulation or suppository may incorporate water containing, and preferably saturated with, nitrous oxide and such additional excipients and carriers as are conventionally used in the pharmaceutical trade in making up such dosage forms. Alternatively in this form of medicament the nitrous oxide may be dissolved in an oil forming part of the formulation. The oil may in this form be either liquid or semi-solid. Thus, the oil may be one which has a creamy or butter-like consistency at room temperature.

In accordance with a further feature of the present invention the administration medium is preferably nitrous oxide saturated water which further includes at least one essential fatty acid or ester thereof selected from the group consisting of oleic acid, linoleic acid, alpha-linolenic acid, gamma-linolenic acid, arachidonic acid and any of the $C_1$ to $C_6$ alkyl esters thereof. The administration medium may further include eicosapentanoic acid [C20:5ω3] and/or decosahexaenoic acid [C22:5ω3] as additional long chain fatty acids.

Surprisingly, the present inventors now find that both narcotic analgesics and non-narcotic analgesics, also known as non-steroidal anti-inflammatory drugs can advantageously be formulated into novel pharmaceutical compositions with nitrous oxide in solution and administered to mammals, especially humans, or used concomitantly therewith, not only to elicit a more potent analgesic, anti-inflammatory or anti-pyretic response, each according to its own inherent properties, but also to evoke such response more rapidly than possible by administration of the agent alone.

In a further aspect, the present invention provides a novel pharmaceutical composition of matter for use in eliciting an analgesic or anti-inflammatory or anti-pyretic response, said composition comprising an effective analgesic, anti-inflammatory or anti-pyretic amount of a non-narcotic analgesic/non-steroidal anti-inflammatory or anti-pyretic drug or of a narcotic analgesic and an amount of nitrous oxide in solution sufficient to hasten the onset of the analgesic, anti-inflammatory and/or anti-pyretic response or to enhance the analgesic, anti-inflammatory and/or anti-pyretic response.

In yet another aspect, the present invention provides a novel composition of matter for use in eliciting an analgesic response, said composition comprising an effective analgesic amount of an orally analgesically active narcotic agonist or agonist-antagonist and an amount of nitrous oxide in aqueous solution sufficient to hasten the onset of the analgesic response or to enhance the analgesic response.

In another aspect, the present invention provides a novel pharmaceutical composition of matter for use in eliciting an analgesic response, said composition comprising an effective analgesic amount of an orally analgesically active narcotic agonist or agonist-antagonist, an amount of a selected non-narcotic analgesic as defined hereinafter sufficient to enhance analgesia, and an amount of nitrous oxide in aqueous solution sufficient to further enhance analgesia or to hasten its onset.

In all the above aspects the provision of essential fatty acids or esters thereof as set out above as part of such formulations provide yet further aspects of the invention.

Typically, the active ingredients of the compositions of the invention are further associated with a non-toxic pharmaceutically acceptable inert carrier therefor.

In other aspects, the invention provides methods of hastening the onset of an analgesic or anti-inflammatory response and methods of eliciting an enhanced analgesic, anti-inflammatory or anti-pyretic response in a mammal.

DETAILED DESCRIPTION OF THE INVENTION

The non-narcotic analgesics or non-steroidal anti-inflammatory drugs for use in the compositions and methods of the present invention can be selected from the following categories:

[1] the propionic acid derivatives;
[2] the acetic acid derivatives;
[3] the fenamic acid derivatives;
[4] the oxicams;
[5] the salicylic acid derivatives; and
[6] the pyrazolones which has analgesic, anti-inflammatory or anti-pyretic activity.

While some of these compounds are primarily used at the present time as anti-inflammatory agents and others are primarily used as analgesics, it has been suggested that in fact most of the contemplated compounds have both analgesic and anti-inflammatory activity and that many of them also have anti-pyretic activity and can be used at appropriate dosage levels for any one or all of these purposes in the compositions and methods of the present invention. The compounds in groups [1] through [4] above typically contain a carboxylic acid function; however, those acids are sometimes administered in the form of their pharmaceutically acceptable salts, e.g. sodium salts.

Irrespective of the chemical structural nature of the analgesic, anti-inflammatory or anti-pyretic drug it is preferred to utilise anti-inflammatory drugs having a high selectivity for inhibiting COX-2, that is, having a COX-2:COX-1 inhibition activity as close as possible to, or preferably below 1. See in this regard the article by John Vane entitled "Towards a better aspirin", *Nature* Volume 367, Jan. 20, 1994, pages 215 to 216 in which he reports that there is support for the hypothesis that the unwanted side effects such as irritation of the stomach lining and toxic effects on the kidneys of NSAIDs are due to their ability to inhibit COX-1 whereas their anti-inflammatory [therapeutic] effects are due to inhibition of COX-2. Diclofenac, which is reported to have a COX-2:COX-1 activity ratio of 2.2 and meloxicam with a ratio of 0.33 are thus clearly the products of choice for this invention.

The propionic acid derivatives for use herein include, but are not limited to, ibuprofen, naproxen, benoxaprofen, flurbiprofen, fenoprofen, fenbufen [sometimes regarded as a butyric acid derivative], ketoprofen, indoprofen, pirprofen, carprofen, oxaprozin, pranoprofen, suprofen, alminoprofen, tiaprofenic acid and bucloxic acid. Structurally related propionic acid derivatives having similar analgesic and anti-inflammatory properties are also intended to be encompassed by this group. Presently preferred members of the propionic acid group include ibuprofen, naproxen, flurbiprofen, fenoprofen, ketoprofen and fenbufen.

Thus, "propionic acid derivatives" as defined herein are non-narcotic analgesics/non-steroidal anti-inflammatory drugs having a free —CH(CH$_3$)COOH or —CH$_2$CH$_2$COOH group [which optionally can be in the form of a pharmaceutically acceptable salt group, e.g. —CH(CH$_3$)COO$^-$Na$^+$ or —CH$_2$CH$_2$COO$^-$Na$^+$), typically attached directly or via a carbonyl function to a ring system, preferably to an aromatic ring system.

The acetic acid derivatives for use herein include, but are not limited to, indomethacin, sulindac, tolmetin, zomepirac, diclofenac, alclofenac, ibufenac, isoxepac, acemetacin, fentiazac and clidanac. Structurally related acetic acid derivatives having similar analgesic and anti-inflammatory properties are also intended to be encompassed by this group. Presently preferred members of the acetic acid group include tolmetin sodium, zomepirac sodium, sulindac, indomethacin and, in particular, diclofenac sodium.

Thus, "acetic acid derivatives" as defined herein are non-narcotic analgesics/non-steroidal anti-inflammatory drugs having a free —CH$_2$COOH group [which optionally can be in the form of a pharmaceutically acceptable salt group, e.g. —CH$_2$COO$^-$Na$^+$], typically attached directly to a ring system, preferably to an aromatic or heteroaromatic ring system.

The fenamic acid derivatives for use herein include, but are not limited to, mefenamic acid, meclofenamic acid, flufenamic acid, niflumic acid and tolfenamic acid. Structurally related fenamic acid derivatives having similar analgesic and anti-inflammatory properties are also intended to be encompassed by this group. Presently preferred members of the fenamic acid group include mefenamic acid and meclofenamate sodium, in particular meclofenamic acid, sodium salt.

Thus, "fenamic acid derivatives" as defined herein are non-narcotic analgesics/non-steroidal anti-inflammatory drugs which contain the basic structure

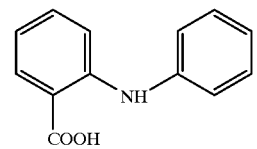

which can bear a variety of substituents and in which the free —COOH group can be in the form of a pharmaceutically acceptable salt group, e.g. —COO$^-$NA$^+$.

The oxicams for use herein include, but are not limited to, meloxicam, piroxicam and isoxicam. Structurally related oxicams having similar analgesic and anti-inflammatory properties are also intended to be encompassed by this group. A preferred member of this group is piroxicam.

Thus, "oxicams" as defined herein are non-narcotic analgesics/non-steroidal anti-inflammatory drugs which have the general formula

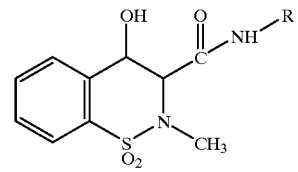

wherein R is an aryl or heteroaryl ring system.

The salicylic acid derivatives for use herein include, but are not limited to, aspirin, diflusinal, salacetamide, salicylamide.

The pyrazolones for use herein include but are not limited to phenylbutazone.

Also according to the present invention there are provided pharmaceutical compositions of matter adapted to elicit an onset hastened and enhanced analgesic and anti-inflammatory response in a mammalian organism in need of such treatment, said composition comprising a unit dosage analgesically and anti-inflammatorily effective amount of an active drug component and an active drug potentiating adjuvant thereof, said active drug comprising a narcotic analgesic or an NSAID selected from the group consisting of the propionic, acetic, fenamic, and salicylic acid derivatives, the oxicams, the pyrazolones and pharmaceutically acceptable salts thereof, and said adjuvant consisting essentially of an active drug analgesic and anti-inflammatory onset hastening and enhancing amount of nitrous oxide in solution in a pharmaceutically acceptable liquid or solid or semi-solid solvent.

Also provided consistent herewith is an advantageous method of eliciting an onset hastened and enhanced analgesic and anti-inflammatory response in a mammalian organism in need of such treatment, comprising administering to such organism a unit dosage analgesically and anti-inflammatorily effective amount of a pharmaceutical composition of matter comprising an active drug component and an active potentiating adjuvant therefor, said active drug comprising a narcotic analgesic or an NSAID selected from the group consisting of the propionic, acetic, fenamic and salicylic acid derivatives, the oxicams, the pyrazolones and pharmaceutically acceptable salts thereof, said adjuvant consisting essentially of an active drug analgesic and anti-inflammatory onset hastening and enhancing amount of nitrous oxide in solution in a pharmaceutically acceptable liquid or solid or semi-solid solvent.

The anti-inflammatory agent may also comprise a glucocorticoid, for example, prednisole.

The narcotic analgesics for use in the present invention are orally active narcotic agonists and narcotic agonist-antagonists [i.e. antagonists with analgesic properties]. Suitable narcotic agonists for use herein include orally analgesically active members of the morphine group, the meperidine group and the methadone group, notably codeine, oxycodone, hydromorphone, levorphanol, meperidine, propoxyphene and methadone. Suitable agonist-antagonists for use herein include orally analgesically active antagonists of the morphine type, notably propiram and buprenorphine; and orally analgesically active antagonists of the nalorphine type, notably pentazocine, nalbuphine and butorphanol. Another suitable agonist-antagonist is meptazinol. In many instances, the narcotic analgesics for use herein are administered in the form of their pharmaceutically acceptable acid addition salts, e.g. codeine sulfate, codeine phosphate, oxycodone hydrochloride, oxycodone terephthalate, hydromorphone hydrochloride, levorphanol tartrate, meperidine hydrochloride, propoxyphene napsylate, methadone hydrochloride, propiram fumarate, buprenorphine hydrochloride, nalbuphine hydrochloride and meptazinol hydrochloride. Further narcotic analgesics which may be used according to this invention include dipipanone, fentanyl, hydrocodone, papaveretum and tilidine.

Further non-narcotic analgesics, not mentioned as anti-inflammatory agents above, which may be used in accordance with the present invention comprise acetaminophen [also known as paracetamol], bufexamac, phenacetin.

Some of the products mentioned above are also antipyretics, such as acetaminophen and indomethacin and may be used for that purpose according to the invention as may other anti-pyretics such as phenacetin.

The term "selected NSAID" as used herein is intended to mean any non-narcotic analgesic/non-steroidal anti-inflammatory compound falling within one of the six structural categories indicated hereinabove. Similarly, the term "selected narcotic analgesic" as used herein is intended to mean any orally analgesically active narcotic agonist or a narcotic antagonist having oral analgesic activity. The terms "selected NSAID" and "selected narcotic analgesic" are used for the sake of simplicity in the discussion which follows.

When a selected NSAID [or selected narcotic or non-narcotic analgesic or anti-pyretic] is combined with nitrous oxide in accordance with the present invention, the following unexpected results are produced:

[1] the analgesic or anti-inflammatory effect of the selected NSAID [or selected narcotic or non-narcotic analgesic or anti-pyretic] on the mammal is brought on more quickly;

[2] lower amounts of the selected NSAID [or selected narcotic or non-narcotic analgesic or anti-pyretic] are required for the same analgesic or anti-pyretic anti-inflammatory effect; and

[3] across all doses, a greater analgesic, anti-inflammatory or anti-pyretic response is achieved.

For patients suffering pain, the time from administration of medication to the onset of effective relief is clearly of paramount importance. The present inventors' discovery that nitrous oxide in solution substantially shortens the onset time [i.e. substantially hastens the onset] of analgesia is therefore very significant; moreover, it is completely unexpected. Likewise, in patients suffering inflammation, e.g. from rheumatoid arthritis or osteoarthritis, the substantial shortening of onset time provided by this invention is extremely important, not only because it provides faster relief from pain but also because it provides more rapid relief from other aspects of the inflammatory disease, e.g. morning stiffness.

Further, the ability of nitrous oxide to enhance analgesia or to enhance the anti-inflammnatory response, i.e. to substantially reduce the amount of the selected NSAID [or selected narcotic or non-narcotic analgesic or anti-pyretic] which is required to elicit a given analgesic, anti-inflammatory or anti-pyretic response, is also an unexpected and very important aspect of this invention. This unexpected and important finding permits the use of the selected NSAID [or selected narcotic or non-narcotic analgesic or anti-pyretic] in quantities substantially less than the dosages presently suggested as an analgesic, anti-inflammatory or anti-pyretic agent in humans. Use of lower doses should in turn lower the incidence and/or severity of undesirable side effects. Moreover, at a given dosage level, greater analgesic, anti-inflammatory or anti-pyretic response can be achieved.

While the compositions of the invention are preferably for oral use, they may also be formulated for and administered by other methods which are known for administering analgesics, e.g. as suppositories, creams, ointments, transdermal pads, buccal pads, or nasally.

The compositions of the present invention are very conveniently administered to mammals by any route of administration suitable for the selected NSAID and/or selected narcotic analgesic component, e.g. oral, rectal or transdermal. Preferably, the combination is formulated with any suitable non-toxic pharmaceutically acceptable inert carrier material. Such carrier materials are well known to those skilled in the art of pharmaceutical formulations. For those not skilled in the art, reference is made to the test entitled "REMINGTON'S PHARMACEUTICAL SCIENCES" [Fourteenth Edition], 1970. In a typical preparation for oral administration, e.g. tablet or capsule, the selected NSAID in an effective analgesic or anti-inflammatory amount and nitrous oxide in an amount sufficient to enhance the analgesic or anti-inflammatory response or to hasten its onset, or the selected narcotic or non-narcotic analgesic in an effective analgesic amount and nitrous oxide in an amount sufficient to enhance the analgesic response or to hasten its onset, or the selected narcotic analgesic in an effective analgesic amount together with a selected NSAID in an amount sufficient to enhance the analgesic response and nitrous oxide in an amount sufficient to further enhance the analgesic response or to hasten its onset, are combined with any oral non-toxic pharmaceutically acceptable inert carrier such as lactose, starch [pharmaceutical grade], dicalcium phosphate, calcium sulfate, kaolin, mannitol and powdered sugar. Additionally, when required, suitable binders, lubricants, disintegrating agents and colouring, flavouring and fragrance agents can also be included. Typical binders include starch, gelatin, sugars such as sucrose, molasses and lactose, natural and synthetic gums such as acacia, sodium alginate, extract of Irish moss, carboxymethyl-cellulose, methylcellulose, polyvinylpyrrolidone, polyethylene glycol, ethylcellulose and waxes. Typical lubricants for use in these dosage forms can include, without limitation, boric acid, sodium benzoate, sodium acetate, sodium chloride, leucine and polyethylene glycol. Suitable disintegrators can include, without limitation, starch, methylcellulose, agar, bentonite, cellulose, wood products, alginic acid, guar gum, citrus pulp, carboxymethylcellulose and sodium lauryl sulfate. If desired, a conventional pharmaceutically acceptable dye can be incorporated into the dosage unit form, i.e. any of the standard FD&C dyes. Sweetening and flavouring agents and preservatives can also be included, particularly when a liquid dosage form is formulated, e.g. an elixir, suspension or syrup. Also, when the dosage form is a capsule, it may contain, in addition to materials of the above type, a liquid carrier such as a fatty oil. Various other materials may be present as coatings or to otherwise modify the physical form of the dosage unit. For instance, tablets, pills or capsules may be coated with shellac, sugar or both. Such active components; generally, the active ingredients will be between about 2% to about 60% of the weight of the unit.

According to the present invention there is particularly provided a topical application formulation comprising a mixture of at least one non-steroidal anti-inflammatory agent, at least one essential fatty acid or ester thereof consisting of oleic acid, linoleic acid, alpha-linolenic acid, gamma-linolenic acid, arachidonic acid and the lower alkyl esters thereof, and nitrous oxide dissolved in a dermatologically acceptable carrier.

In this regard it has surprisingly been found that the compound diclofenac sodium, which is known to be relatively inactive in a topical application form, can be used in this formulation to bring rapid and long-lasting relief to a large variety of painful conditions by the application of a relatively low dosage of the active ingredient.

The term lower alkyl esters as used herein is intended to denote esters in which the alcohol moiety has up to six carbon atoms.

In the preferred form of the invention the composition is saturated with nitrous oxide.

Also, in the preferred form of the invention the essential fatty acid component of the composition comprises a mixture of esters of the fatty acids listed above. Thus, in the most preferred form of the invention the fatty acid component of the composition is constituted by the complex known as Vitamin F and in this regard it is preferred to make use of the ester form of Vitamin F known as Vitamin F Ethyl Ester. This product is commercially available under the trade description of Vitamin F Ethyl Ester CLR 110 000 Sh.L. U./g from CLR Chemicals Laboratorium Dr. Kurt Richter GmbH of Berlin, Germany. The typical fatty acid distribution of this product is as follows:

| | | |
|---|---|---|
| <$C_{16}$ | : | 0% |
| $C_{16-0}$ | : | 8,3% |
| $C_{18-0}$ | : | 3,5% |
| $C_{18-1}$ | : | 21,7% |
| $C_{18-2}$ | : | 34,8% |
| $C_{18-3}$ | : | 28,0% |
| >$C_{18}$ | : | 1,6% |
| unknown | : | 2,1% |

It is further preferred to add to the formulation the long chain fatty acids known as eicosapentanoic acid [$C20:5\omega3$] and decosahexaenoic acid [$C22:5\omega3$]. Such a product combination is available from Roche Lipid Technology under the trade name "Ropzifa '30' n-3 oil".

EXAMPLES OF THE INVENTION

Without thereby limiting the scope of the invention some examples will now be described to illustrate the invention.

Example 1

Preparing a Nitrous Oxide Solution

A pressure vessel is charged to its operating volume with water at 20° C. [ambient temperature]. The vessel is connected to a supply of nitrous oxide via a flow control valve and pressure regulator. The closed vessel is supplied with nitrous oxide at a pressure of 2 bar for a period of 48 hours, it having been determined that at the aforementioned temperature the water is saturated with nitrous oxide over such period of time under the above-mentioned pressure.

A resultant solution is bottled as stock solution for use in the formulations and applications set out below.

Example 2

Preparation of Nitrous Oxide/Vitamin F Emulsion 30 g Vitamin F ethyl ester as described above was mixed with 10 g chremaphor, 2,2 g methyl paraben, 0,08 g butyl hydroxyanisole, 0,23 g butyl hydroxytoluene with stirring at 80° C.

Into 942,5 g of the stock nitrous oxide solution was dissolved 2,5 g sodium propyl paraben and 2,5 g Gennall 115 [Imidurea] with stirring at room temperature.

The oily composition first described was emulsified into the aqueous solution with stirring to constitute a stock nitrous oxide/Vitamin F emulsion.

Example 3

Preparation of an Indomethacin-containing Topical Lotion

One gram indomethacin was included in the stock nitrous oxide/Vitamin F emulsion as described in Example 2 above by the addition thereof to the oily composition before the latter was emulsified into the aqueous solution. Keltrol [about 9 g] was added to the final composition as a thixotropic agent to obtain the desired thickness of the emulsion.

The amounts of the other ingredients were recalculated for a final formulation having a concentration of 0,1% indomethacin, that is 1 mg/g.

Example 4

Preparation of an Ibuprofen-containing Formulation

An ibuprofen-containing formulation was prepared in the same manner as described in Example 3 by introducing 8 g of ibuprofen instead of 1 g indomethacin and using 935,5 g of stock nitrous oxide solution.

This resulted in a formulation containing 8 mg/g ibuprofen.

Example 5

Preparation of a Diclophenac Sodium Formulation

A diclophenac preparation was prepared in the same manner as described in Example 3, save that 10.8 g diclophenac sodium was added to the aqueous nitrous oxide solution rather than indomethacin to the oil. Quantities of other ingredients were again adjusted to yield a resultant preparation containing 10.8 mg/g diclophenac sodium, that is 1 g/100 g diclofenac expressed as base.

Example 6

Preparation of a Dental Pad

The indomethacin-containing emulsion as prepared according to Example 3 but without any Keltrol was impregnated onto strips cut from a woven cotton pad of the type used as a cosmetic cleansing pad. Each strip was 50 mm long and 10 mm high and was impregnated with 0,5 ml of the emulsion of Example 3 sans Keltrol. The strips thus each contained 0,5 mg of indomethacin. The impregnated pad was packaged in a sealed PVC sachet.

CLINICAL EVALUATIONS

CASE 1

NITROUS OXIDE WITH ASPIRIN AND CODEINE PHOSPHATE IN THE TREATMENT OF MIGRAINE

A Caucasian woman, aged 25, presenting with recurrent migraine attacks was given two commercially available aspirin tablets [i.e. 1000 mg aspirin+16 mg codeine phosphate] which were crushed and suspended in a glass of stock nitrous oxide solution [as described in Example 1] at the onset of what was expected to be a migraine attack as experienced by dots before the eyes and a mild headache. The headache abated within 10 minutes and no migraine ensued.

Previous attempts to prevent migraine attacks by taking the same aspirin tablets alone in plain water at the same stage of onset proved fruitless for this patient. Likewise, the administration of a nitrous oxide solution alone previously did not prevent an attack.

CASE 2

NITROUS OXIDE, VITAMIN F AND INDOMETHACIN IN A TOPICAL APPLICATION FOR THE TREATMENT OF PSORIATIC ARTHRITIS

A 50 year old Caucasian female patient suffering from psoriatic arthritis had previously been treated with gold injections, diclophenac sodium injections, cortisone injection, and hospitalisation. She had very little relief from these treatments and had great difficulty in walking.

The formulation of Example 3 above was applied 4 hourly to the affected joints and after two days of such treatment there was a visible reduction of the swelling of the joints and she managed to undertake walks in excess of 1 kilometre with a natural gait.

The relief was transient and treatment had to continue to maintain her improved condition. She reported that the formulation was clearly much more efficient than commercially available ointments containing indomethacin in a quantity of 10 mg/g, i.e. 10 times that of the preparation of the invention.

CASE 3

NITROUS OXIDE, VITAMIN F AND IBUPROFEN IN A TOPICAL APPLICATION FOR THE TREATMENT OF ARTHITIS AND BACKACHE

A Caucasian male in his late 40's who had undergone four knee operations as a result of being afflicted with arthritis was also suffering from such severe backache that he seldom enjoyed more than 1 to 2 hours sleep at night.

The formulation of Example 4 above was applied to his back as a lotion once every four hours and he reported a measure of relief within a day. He managed to go for a week without the need of further treatment after treatment on the first day.

He had previously not experienced the same or even a comparable measure of relief when using commercially available diclophenac formulation of much higher [typically 116 mg/g] concentration of diclophenac, i.e. more than 10 times the concentration found in the preparation of the invention.

CASE 4

NITROUS OXIDE, VITAMIN F AND IBUPROFEN IN BUCCAL APPLICATION FOR TREATMENT OF PERIODONTAL PAIN

A male Caucasian in his early 40's suffered severe pain following periodontal surgery. The pad of the type described in Example 6 but containing 8 mg ibuprofen rather than 0,5 mg indomethacin was applied to the gums at the affected area and the pain subsided within minutes.

This result is particularly remarkable in view of the fact that the patient had 4 hours before this treatment taken 2 tablets of a commercially available oral preparation each containing ibuprofen 200 mg, paracetamol 250 mg and codeine phosphate 10 mg and had not experienced significant pain reduction.

CASE 5

NITROUS OXIDE, VITAMIN F AND INDOMETHACIN IN BUCCAL APPLICATION FOR TREATMENT OF INFLAMMATION OF GUMS

A random sample of 10 volunteers experiencing simple inflammation of the gums post dental treatment were selected. Each patient was handed six [6] impregnated strips as described in Example 6 above with the following instructions:

[1] Place strip against inflamed area and retain until pain subsides.
[2] Measure and record the exact time taken to experience complete pain relief.
[3] Measure and record the duration of analgesic effect after each single application.
[4] Record any untoward effects.
[5] Record any effects other than reduction of pain.
[6] Assess and record effect on swelling.

[7] Repeat if pain recurs.
Findings
  The result of the trial are recorded in Tables 1 and 2.
  From Table 1 below the following are apparent:
[1] The average time required for full analgesia was 53 seconds.
[2] The effective time of full analgesia reduced progressively with succeeding applications.
[3] Only three patients required a sixth application.
[4] The average total drug delivery was 2,5 mg per patient.

TABLE 1

| Patient | Time Required for Analgesic Effect (Seconds) | | | | | |
|---|---|---|---|---|---|---|
| Number | 1st | 2nd | 3rd | 4th | 5th | 6th |
| 1 | 45 | 50 | 45 | | | |
| 2 | 55 | 45 | 65 | 55 | 40 | |
| 3 | 65 | 60 | 65 | 55 | 45 | 45 |
| 4 | 35 | 40 | 35 | 45 | | |
| 5 | 95 | 80 | 85 | 90 | 75 | |
| 6 | 50 | 45 | 40 | 40 | 35 | |
| 7 | 45 | 50 | 45 | 45 | 40 | 40 |
| 8 | 70 | 70 | 65 | 70 | 60 | 65 |
| 9 | 45 | 50 | 45 | 40 | 35 | |
| 10 | 50 | 60 | 75 | 50 | 45 | |
| Average | 55.5 | 55 | 56.5 | 54.44 | 46.88 | 50 |

From table 2 below the following are apparent:
[1] The average period of duration of analgesia was 7.2 hours per application.
[2] The average period of duration of analgesic effect increased by 41% from 5.78 hours at first application to 8.17 hours for the last application.
[3] On average, the total period of treatment required was 36.6 hours which translates into 1.5 days in treatment.
[4] The total daily requirement of indomethacin per patient was therefore 1,67 mg.

TABLE 2

| Patient | Duration of Analgesic Effect (Hours) | | | | | |
|---|---|---|---|---|---|---|
| Number | 1st | 2nd | 3rd | 4th | 5th | 6th |
| 1 | 5.5 | 7 | 10 | | | |
| 2 | 4 | 5 | 5.5 | 6.75 | 7.25 | |
| 3 | 6.5 | 5 | 7.5 | 7.25 | 8 | 9.5 |
| 4 | 6 | 6.5 | 7.5 | 10.5 | | |
| 5 | 4 | 4 | 5.5 | 7 | 9.5 | |
| 6 | 6.75 | 7.25 | 7.25 | 8.5 | 8.75 | |
| 7 | 6.5 | 6 | 7 | 7.25 | 6.5 | 7.5 |
| 8 | 4.5 | 6 | 5.5 | 7 | 7.25 | 7.5 |
| 9 | 6.5 | 5 | 7 | 7.5 | 7.75 | |
| 10 | 7.5 | 8.5 | 8 | 9.5 | 10 | |
| Average | 5.78 | 6.03 | 7.08 | 7.92 | 8.13 | 8.17 |

In general, the following patient observations have been made:
[1] No side-effects have been experienced.
[2] A slight numbness was experienced by 7 of the patients. The duration thereof was limited to a few minutes. This was, however, considered to be an acceptable side-effect as it contributed to the feeling of comfort.
[3] In all patients there was a considerable reduction of inflammation and only 2 patients required treatment in excess of the experimental six applications.
Conclusions
  From the above the following are apparent:
[1] There is every reason to believe that this modality of treatment provides an effective lower dose alternative to the oral administration of NSAID's in the treatment of inflammation of the buccal area.

[2] Although no control group using conventional treatment has been used in this experiment, experience has led us to believe that the efficacy of this treatment is considerably superior to the conventional.

CASE 6

NITROUS OXIDE, VITAMIN F AND DICLOFENAC SODIUM IN TOPICAL APPLICATION FOR THE TREATMENT OF MIGRAINE

A 48 year old female Caucasian who had a long history of migraine attacks which had been quite severe and quite often associated with visual disturbances as well as photo- and phonophobia was seen by a specialist neurologist when she had an attack of migraine and was in considerable distress. The attack was associated with her period and some dysmenorrhoea. She was given the diclofenac sodium formulation of Example 5 from which she applied about 5 cc over the temples, over the frontal areas and over the upper nuchal and occipital areas. The formulation was re-applied over the same areas ten minutes later and within fifteen minutes thereafter and with some surprise, she indicated that the pain had completely disappeared.

On previous occasions she had taken 2 Disprins® [each containing 300 mg aspirin] at the onset of migraine symptoms and mostly this would result in relief after about thirty minutes. This treatment had not always been successful.

CASE 7

NITROUS OXIDE, VITAMIN F AND DICLOFENAC SODIUM IN TOPICAL APPLICATION FOR THE TREAT OF MIGRAINE

Another female Caucasian patient aged 53 of the same specialist neurologist referred to in case 6 above has suffered from typical migraine headaches since her early 20's and over the past 2 to 3 years these had occurred at irregular intervals, from about 3 or 4 to 1 per month. There were no obvious precipitating factors and at the onset she would have nausea and mild visual disturbances with photophobia.

During a typical migraine attack with the pain mainly over the R-nuchal and occipital region, but also the R-temple and frontal areas, and after these had already been present for about 20 minutes, she applied the diclofenac formulation of Example 5 to these areas and within twenty minutes her pain had completely subsided.

Previously she had found that Migril® with Voltaren® suppository provided her with the best relief and on average it took about half an hour for the pain to subside. On this occasion such medication was not required.

CASE 8

NITROUS OXIDE, VITAMIN F AND DICLOFENAC SODIUM IN TOPICAL ADMINISTRATION FOR TREADED OF POLYMORPHIC RASH AND INAON FOLLOWING SUNBURN

A 9 year old blond girl with a very pale skin started developing a rash over her chest and shoulders during the summer. This only occurred with sun exposure. The condition was diagnosed as a Polymorphic rash. The condition developed again on exposure, and the following day after she had again been in the sun for a short time this became much more inflamed, very itchy and painful. The diclofenac formulation of Example was applied over the affected areas and within five minutes the itchiness and pain had completely disappeared. By the following day the rash had completely disappeared.

CASE 9

NITROUS OXIDE, VITAMIN F AND DICLOFENAC IN THE TOPICAL TREATMENT OF PAIN RESULTING FROM KNEE SURGERY

A gentleman in his seventies underwent a knee replacement operation and for five weeks thereafter he was still in pain and on crutches, but his main complaint was the discomfort experienced at night. During this period it was necessary to take pain relieving tablets on a regular basis. His sleeping pattern was severely affected resulting in the patient also having to resort to the taking of sleeping tablets. He reported that he experienced very little relief from the use of a commercially available gel formulation containing diclofenac diethylammonniumin a concentration of 1.16 g/100 g, i.e. about 1 g/100 g diclofenac expressed as base.

Within minutes after a first application of the diclofenac sodium preparation of Example 5 he experienced substantial relief and that night, after further application he was able to sleep for periods of two to three hours which was for him a great improvement. This was obtained by merely rubbing a little of the lotion over the knee. After about 3 weeks it was possible to get much longer periods of relief at nights using just the formulation. Since using that formulation he has not had any need to resort to any other sort of medication.

CASE 10

PILOT STUDY ON NITROUS OXIDE, VITAMIN F AND DICLOFENAC SODIUM IN THE TREATMENT OF ARTHROPATHY

A pilot, uncontrolled study on the effects of the diclofenac sodium formulation of Example 5 on patients suffering from arthropathy resulting from various causes was conducted by a rheumatologist of many years standing. The patients were selected from his extensive practice and most of these have over a period of years tried various preparations.

The formulation of Example 5 was applied in 5 to 15 ml quantities 3 to 4 times per day over the affected parts of the body.

Measurement of effect was by simple patient and physician global assessment and hence had an element of subjectivity. However, the fact that 70% of the patients reported a positive result [33% being "much better" and 37% being "better"] attributed to the treatment is highly significant bearing in mind that most of these patients had the symptoms for many years. Some of the patients reported a dramatic improvement while only two patients reported being worse after the treatment.

The investigating rheumatologist noted that side effects were minimal and remarked that a particular impression of the product was its apparent rapid onset of action—a particular advantage in the treatment of patients with the conditions in issue.

These positive results had lead to the applicant's current planning a full scale properly controlled trial of the preparation on patients suffering from osteoarthritis and rheumatoid arthritis.

CASE 11

NITROUS OXIDE, VITAMIN F AND MEFENAMIC ACID IN ORAL FORMULATON FOR THE TEATMENT OF FEVER AND PAIN

A suspension for oral administration comprising mefenamic acid in the stock nitrous oxide/Vitamin F emulsion of Example 2 was made up so that the concentration was just 15 mg/5 ml, i.e. substantially less than the 50 mg/5 ml present in commercially available mefenamic acid preparations.

The preparation was administered to three children aged from 9 to 12 years instead of the proprietary brand containing Mefenamic acid that they normally used. The conditions for which the medicine was given ranged from fever to pain and headache and the dose was given as if it were the higher concentration proprietary product.

In all cases the onset of pain relief and reduction of fever was shorter than that experienced with the proprietary preparation.

The duration of action was of the same order as the proprietary brand.

In one case only the subject required more than two administrations during a 24 hour period, however the total drug delivery was still lower than that normally given with the proprietary brand.

This provides a strong indication that the drug is more highly absorbed and therefore a lower dose can be given for the same or better effects.

CASE 12

NITROUS OXIDE, VITAMIN F AND NAPROXEN IN A TOPICAL APPLICATION FOR THE TREATMNT OF JOINT ACHES AND SPORT INJURIES

A topical preparation containing 5% naproxen in the emulsion of Example 2 was made up and used on 3 patients who suffered from rheumatic joint problems and also on two patients who had suffered low grade sport injuries, one to the knee and one to the shoulder. All of the patients with rheumatic joint problems reported an increase in mobility of the affected joints, reduction of pain and a marked reduction of swelling.

One of the patients felt that this treatment gave better effects than that after intra-articular steroid injections. The other two patients felt that the effects were equal to their normally orally administered anti-inflammatories.

Compliance was better with all these patients who normally received orally administered NSAID's as they did not experience the gastric side effects with the topical product.

Both the patients with the sports injuries were able to resume their normal activities within two days from starting application of product. The relief of pain was achieved within the first 15 minutes and sustained for approximately six hours.

The first patient, who had suffered a knee injury [from bicycling] was able to walk without a limp on the second day, but felt unready to resume bicycling at that time.

The second patient, who suffered an exacerbation of a shoulder injury [from archery] was able to resume his sport within a week. He reported that previously in such a situation neither oral or topical NSAID's or other medications or procedures other than total inactivity would allow this resumption, and then only after some weeks.

CASE 13

NITROUS OXIDE, VITAMIN F AND SULINDAC IN A TOPICAL PREPARATION FOR THE TREATMENT OF PSORIATIC ARTHROPATHY

A topical preparation containing 5% sulindac in the emulsion of Example 2 was made up and used on patients that suffered from psoriatic arthropathy.

These patients, having already had experience of topically applied NSAID's as well as orally administered NSAID's, felt that the effects of the above test material were similar to that of the orally administered products, better than that of the topically administered products and quicker in onset of action than any of the previously tried products.

Duration of action was considerably longer than that of other topically applied NSAID's. Duration of action as compared to orally administered medications was difficult to ascertain as their normal oral medication included long acting once a day preparations. The total drug delivery of the test material per day on a comparative basis with the long acting oral preparations was much lower and the patients felt that this lower systemic dose would help them comply with treatment.

CASE 14

NITROUS OXIDE, VITAMIN F AND DIFLUSINAL IN A TOPICAL PREPARATION FOR USE IN THE TREATMENT OF PSORIATIC ARTHROPATHY, RHEUMATOID ARTHRITIS AND SUNBURN INFLAMMATION

A topical preparation containing 3% diflusinal in the suspension of Example 2 was made up and used on patients that suffered from psoriatic arthropathy, rheumatoid arthritis and inflammation due to sunburn.

One patient with rheumatoid arthritis of both hands reported a lessening of pain and a visible increase in mobility of both wrist joints within two minutes of application. She was able to resume her job of collating paperwork at a printing firm without pain the same day. Previously she required intra-articular corticosteroid injections to her wrist joint and to the joint between the first and second fingers. The pain of these injections made her reluctant to continue therapy.

Two patients with inflammation due to severe sunburn reported a total cession of pain with a single application of this composition. There was no need for re-application until awakening the next day, and then only as a measure "just in case", as the redness was not totally removed. None of the patients developed blisters.

Patients with psoriatic arthropathy experienced similar effects to that experienced with the sulindac test material, with no discernible differences.

CASE 15

NITROUS OXIDE, VITAMIN F AND MELOXICAM IN ORAL ADMINISTRATION FOR THE TREATMENT OF ABDOMINAL PAIN

A patient suffering abdominal pain resulting from postoperative abdominal adhesions regularly took two commercially available tablets containing meloxicam as active ingredient for pain relief. This patient experienced much more rapid onset of the pain relief when these tablets were crushed as swallowed down with 15 ml of the nitrous oxide/Vitamin F emulsion of Example 2, than when swallowed with ordinary water, even using crushed tablets. This was also his experience when swallowing the crushed meloxicam tablets with a saturated solution of nitrous oxide in water.

EXPERIMENTAL

In Vitro Release of Diclofenac Sodium from the Preparation of Example 5

The in vitro release of diclofenac sodium from the lotion of the preparation made as described in Example 5 was measured with a set-up related to USP dissolution apparatus. The reservoir of the dissolution cell [enhancer cell] was filled according to the prescribed procedure with the lotion and the lotion was covered with the membrane [cellulose acetate; 0.4 $\mu$m pore size], taking care to exclude air bubbles between the lotion and the membrane. The cell was capped and placed in the dissolution vessel containing the receptor medium [pH 6.8 phosphate buffer; 190 ml]. The paddle speed was 100 rpm. Samples of 250 $\mu$l were withdrawn with a micropipette at 30, 60, 120, 240 and 360 minutes. The samples were analysed for diclofenac by means of HPLC.

RESULTS

The release experiment was done six fold and the average release was calculated for each analysis point.

The release rate [or flux] of diclofenac sodium from the formulation was determined to be 122 $\mu g/cm^2/min^{0.5}$ which is considered to be very high since the release rate of active ingredients from most creams, irrespective of the active ingredient typically about 10 times lower, i.e. about 10 $\mu g/cm^2/min^{0.5}$. This high release rate may well contribute to the reported rapid onset of relief referred to above. The mechanism of absorption is however not yet understood but it is clear that the formulation of the invention allows rapid release of the active ingredient and hence rapid availability for absorption through the skin.

What is claimed is:

1. A method of enhancing or more rapidly eliciting an analgesic, anti-inflammatory and/or anti-pyretic response in a patient, the method comprising administering to the patient a pharmaceutical composition comprising an analgesic, anti-inflammatory and/or anti-pyretic response-producing effective amount of a medicament, and a pharmaceutically acceptable solution containing nitrous oxide, wherein the nitrous oxide is present in an amount such that the analgesic, anti-inflammatory and/or anti-pyretic response is enhanced in the patient or more rapidly elicited in the patient, as compared to a method of administering a same amount of an identical pharmaceutical composition which lacks the nitrous oxide.

2. The method of claim 1, wherein the medicament comprises a member selected from the group consisting of a propionic acid derivative, an acetic acid derivative, a fenamic acid derivative, a salicylic acid derivative, an oxicam derivative and a pyrazolone derivative.

3. The method of claim 2, wherein the medicament comprises a propionic acid derivative selected from the group consisting of ibuprofen, naproxen, benoxaprofen, flurbiprofin, fenoprofen, fenbufen, ketoprofen, indoprofen, pirprofen, carprofen, oxaprozin, pranoprofen, suprofen, alminoprofen, tiaprofenic acid and bucloxic acid, or a pharmaceutically acceptable salt thereof.

4. The method of claim 3, wherein the propionic acid derivative is selected from the group consisting of ibuprofen, naproxen, flurbiprofin, fenoprofen, fenbufen and ketoprofen, or a pharmaceutically acceptable salt thereof.

5. The method of claim 2, wherein the medicament comprises an acetic acid derivative selected from the group consisting of indomethacin, sulindac, tolmetin, zomepirac, diclofenac, alclofenac, ibufenac, isoxepac, acemetacin, fentiazac and clidanac, or a pharmaceutically acceptable salt thereof.

6. The method of claim 5, wherein the acetic acid derivative is selected from the group consisting of tolmetin, zomepirac, sulindac, indomethacin and diclofenac, or a pharmaceutically acceptable salt thereof.

7. The method of claim 2, wherein the medicament comprises a fenamic acid derivative selected from the group consisting of mefenamic acid, meclofenamic acid, flufenamic acid, niflumic acid and tolfenamic acid, or a pharmaceutically acceptable salt thereof.

8. The method of claim 7, wherein the fenamic acid derivative is selected from the group consisting of mefenamic acid and meclofenamic acid, or a pharmaceutically acceptable salt thereof.

9. The method of claim 2, wherein the medicament comprises an oxicam derivative selected from the group consisting of meloxicam, piroxicam and isoxicam, or a pharmaceutically acceptable salt thereof.

10. The method of claim 2, wherein the medicament comprises a salicylic acid derivative selected from the group consisting of aspirin, diflusinal, salacetamide and salicylamide, or a pharmaceutically acceptable salt thereof.

11. The method of claim 2, wherein the medicament comprises a pyrazolone derivative.

12. The method of claim 1, wherein the medicament comprises a member selected from the group consisting of acetaminophen, bufexamac and phenacetin.

13. The method of claim 1, wherein the solution is saturated with nitrous oxide.

14. The method of claim 1, wherein the solution comprises water which is saturated with nitrous oxide.

15. A method of enhancing or more rapidly eliciting an analgesic response in a patient, the method comprising
administering to the patient a pharmaceutical composition comprising
an analgesic response-producing effective amount of a medicament comprising a narcotic agonist or agonist-antagonist, and
a pharmaceutically acceptable solution containing nitrous oxide, wherein the nitrous oxide is present in an amount such that the analgesic response is enhanced in the patient or more rapidly elicited in the patient, as compared to a method of administering a same amount of an identical pharmaceutical composition which lacks the nitrous oxide.

16. The method of claim 15, wherein the medicament comprises a member selected from the group consisting of morphine, codeine, oxycodone, hydromorphone, levorphanol, meperidine, propoxyphene, methadone, propiram, buprenorphine, nalorphine, pentazocine, nalbuphine, butorphanol, meptazinol, dipipanone, fentanyl, hydrocodone, papaveretum and tilidine, or a pharmaceutically acceptable salt thereof.

17. The method of claim 15, wherein the solution is saturated with nitrous oxide.

18. The method of claim 15, wherein the solution comprises water which is saturated with nitrous oxide.

19. A method of enhancing or more rapidly eliciting an analgesic response in a patient, the method comprising
administering to the patient a pharmaceutical composition comprising
an analgesic response-producing effective amount of a first medicament comprising a narcotic agonist or agonist-antagonist,
an analgesic response-enhancing effective amount of a second medicament comprising a non-narcotic analgesic, and
a pharmaceutically acceptable solution containing nitrous oxide, wherein the nitrous oxide is present in an amount such that the analgesic response is enhanced in the patient or more rapidly elicited in the patient, as compared to a method of administering a same amount of an identical pharmaceutical composition which lacks the nitrous oxide.

20. The method of claim 19, wherein the first medicament comprises a member selected from the group consisting of morphine, codeine, oxycodone, hydromorphone, levorphanol, meperidine, propoxyphene, methadone, propiram, buprenorphine, nalorphine, pentazocine, nalbuphine, butorphanol, meptazinol, dipipanone, fentanyl, hydrocodone, papaveretum and tilidine, or a pharmaceutically acceptable salt thereof.

21. The method of claim 19, wherein the second medicament comprises a member selected from the group consisting of a propionic acid derivative, an acetic acid derivative, a fenamic acid derivative, a salicylic acid derivative, an oxicam derivative and a pyrazolone derivative.

22. The method of claim 21, wherein the second medicament comprises a member selected from the group consisting of ibuprofen, naproxen, benoxaprofen, flurbiprofin, fenoprofen, fenbufen, ketoprofen, indoprofen, pirprofen, carprofen, oxaprozin, pranoprofen, suprofen, alminoprofen, tiaprofenic acid, bucloxic acid, indomethacin, sulindac, tolmetin, zomepirac, diclofenac, alclofenac, ibufenac, isoxepac, acemetacin, fentiazac, clidanac, mefenamic acid, meclofenamic acid, flufenamic acid, niflumic acid, tolfenamic acid, meloxicam, piroxicam, isoxicam, aspirin, diflusinal, salacetamide, salicylamide, phenylbutazone, acetaminophen, bufexamac and phenacetin, or a pharmaceutically acceptable salt thereof.

23. The method of claim 19, wherein the solution is saturated with nitrous oxide.

24. The method of claim 19, wherein the solution comprises water which is saturated with nitrous oxide.

25. A pharmaceutical composition suitable for producing an analgesic, an anti-inflammatory and/or an anti-pyretic response, the pharmaceutical composition comprising an analgesic, anti-inflammatory and/or anti-pyretic response-producing medicament, and a pharmaceutically acceptable solution containing nitrous oxide in an amount sufficient to produce an enhanced or more rapidly elicited analgesic, anti-inflammatory and/or anti-pyretic response, as compared to a pharmaceutical composition containing a same amount of an identical medicament but lacking the nitrous oxide, with the proviso that the medicament is other than methyl salicylate or arnica.

26. The pharmaceutical composition of claim 25, wherein the medicament comprises a member selected from the group consisting of a propionic acid derivative, an acetic acid derivative, a fenamic acid derivative, a salicylic acid derivative, an oxicam derivative and a pyrazolone derivative.

27. The pharmaceutical composition of claim 24, wherein the medicament comprises a propionic acid derivative selected from the group consisting of ibuprofen, naproxen, benoxaprofen, flurbiprofin, fenoprofen, fenbufen, ketoprofen, indoprofen, pirprofen, carprofen, oxaprozin, pranoprofen, suprofen, alminoprofen, tiaprofenic acid and bucloxic acid, or a pharmaceutically acceptable salt thereof.

28. The pharmaceutical composition of claim 27, wherein the propionic acid derivative is selected from the group consisting of ibuprofen, naproxen, flurbiprofen, fenoprofen, fenbufen and ketoprofen, or a pharmaceutically acceptable salt thereof.

29. The pharmaceutical composition of claim 26, wherein the medicament comprises an acetic acid derivative selected from the group consisting of indomethacin, sulindac, tolmetin, zomepirac, diclofenac, alclofenac, ibufenac, isoxepac, acemetacin, fentiazac and clidanac, or a pharmaceutically acceptable salt thereof.

30. The pharmaceutical composition of claim 29, wherein the acetic acid derivative is selected from the group consisting of tolmetin, zomepirac, sulindac, indomethacin and diclofenac, or a pharmaceutically acceptable salt thereof.

31. The pharmaceutical composition of claim 26, wherein the medicament comprises a fenamic acid derivative selected from the group consisting of mefenamic acid, meclofenamic acid, flufenamic acid, niflumic acid and tolfenamic acid, or a pharmaceutically acceptable salt thereof.

32. The pharmaceutical composition of claim 31, wherein the fenamic acid derivative is selected from the group consisting of mefenamic acid and meclofenamic acid, or a pharmaceutically acceptable salt thereof.

33. The pharmaceutical composition of claim 26, wherein the medicament comprises an oxicam derivative selected from the group consisting of meloxicam, piroxicam and isoxicam, or a pharmaceutically acceptable salt thereof.

34. The pharmaceutical composition of claim 26, wherein the medicament comprises a salicylic acid derivative selected from the group consisting of aspirin, diflusinal, salacetamide and salicylamide, or a pharmaceutically acceptable salt thereof.

35. The pharmaceutical composition of claim 26, wherein the medicament comprises a pyrazolone derivative.

36. The pharmaceutical composition of claim 25, wherein the medicament comprises a member selected from the group consisting of acetaminophen, bufexamac and phenacetin.

37. The pharmaceutical composition of claim 25, wherein the solution is saturated with nitrous oxide.

38. The pharmaceutical composition of claim 25, wherein the solution comprises water which is saturated with nitrous oxide.

39. The pharmaceutical composition of claim 25, further comprising at least one essential fatty acid or a $C_1$–$C_6$ alkyl ester thereof, wherein the at least one essential fatty acid is selected from the group consisting of oleic acid, linoleic acid, alpha-linolenic acid, gamma-linolenic acid and arachidonic acid.

40. The pharmaceutical composition of claim 25, further comprising vitamin F ethyl ester.

41. The pharmaceutical composition of claim 25, further comprising at least one of eicosapentanoic acid and decosahexanoic acid.

42. The pharmaceutical composition of claim 25, wherein the medicament comprises a narcotic agonist or agonist-antagonist.

43. The pharmaceutical composition of claim 42, wherein the medicament comprises a member selected from the group consisting of morphine, codeine, oxycodone, hydromorphone, levorphanol, meperidine, propoxyphene, methadone, propiram, buprenorphine, nalorphine, pentazocine, nalbuphine, butorphanol, meptazinol, dipipanone, fentanyl, hydrocodone, papaveretum and tilidine, or a pharmaceutically acceptable salt thereof.

44. The pharmaceutical composition of claim 25, wherein the medicament comprises a non-narcotic analgesic, and the pharmaceutical composition further comprises a second medicament comprising a narcotic agonist or agonist-antagonist.

45. The pharmaceutical composition of claim 44, wherein the second medicament comprises a member selected from the group consisting of morphine, codeine, oxycodone, hydromorphone, levorphanol, meperidine, propoxyphene, methadone, propiram, buprenorphine, nalorphine, pentazocine, nalbuphine, butorphanol, meptazinol, dipipanone, fentanyl, hydrocodone, papaveretum and tilidine, or a pharmaceutically acceptable salt thereof.

46. The pharmaceutical composition of claim 44, wherein the non-narcotic analgesic comprises a member selected from the group consisting of a propionic acid derivative, an acetic acid derivative, a fenamic acid derivative, a salicylic acid derivative, an oxicam derivative and a pyrazolone derivative.

47. The method of claim 46, wherein the non-narcotic analgesic comprises a member selected from the group consisting of ibuprofen, naproxen, benoxaprofen, flurbiprofin, fenoprofen, fenbufen, ketoprofen, indoprofen, pirprofen, carprofen, oxaprozin, pranoprofen, suprofen, alminoprofen, tiaprofenic acid, bucloxic acid, indomethacin, sulindac, tolmetin, zomepirac, diclofenac, alclofenac, ibufenac, isoxepac, acemetacin, fentiazac, clidanac, mefenamic acid, meclofenamic acid, flufenamic acid, niflumic acid, tolfenamic acid, meloxicam, piroxicam, isoxicam, aspirin, diflusinal, salacetamide, salicylamide, phenylbutazone, acetaminophen, bufexamac and phenacetin, or a pharmaceutically acceptable salt thereof.

48. The method of claim 1, wherein the medicament is other than methyl salicylate or arnica.

49. The method of claim 19, wherein the non-narcotic analgesic is other than methyl salicylate or arnica.

* * * * *